United States Patent
Jones et al.

(10) Patent No.: US 9,149,341 B2
(45) Date of Patent: *Oct. 6, 2015

(54) DEPLOYMENT OF POLYSACCHARIDE MARKERS FOR TREATING A SITE WITHIN A PATIENT

(75) Inventors: Michael L. Jones, San Clemente, CA (US); Paul Lubock, Monarch Beach, CA (US)

(73) Assignee: SenoRx, Inc, Tempe, AZ (US)

( * ) Notice: Subject to any disclaimer, the term of this patent is extended or adjusted under 35 U.S.C. 154(b) by 225 days.

This patent is subject to a terminal disclaimer.

(21) Appl. No.: 13/301,024

(22) Filed: Nov. 21, 2011

(65) Prior Publication Data

US 2012/0116215 A1   May 10, 2012

Related U.S. Application Data

(63) Continuation-in-part of application No. 12/070,786, filed on Feb. 21, 2008, now abandoned, which is a continuation-in-part of application No. 11/881,264, filed on Jul. 26, 2007, now abandoned, application No. 13/301,024, which is a continuation-in-part of application No. 13/155,628, filed on Jun. 8, 2011, now Pat. No. 8,626,269, which is a continuation of application No. 10/444,770, filed on May 23, 2003, now Pat. No. 7,983,734, application No. 13/301,024, which is a continuation-in-part of application No. 13/037,971, filed on Mar. 1, 2011, now Pat. No. 8,361,082, which is a continuation-in-part of application No. 10/753,694, filed on Jan. 7, 2004, now abandoned, which is a continuation-in-part of application No. 10/444,770, filed on May 23, 2003, now Pat. No. 7,983,734, application No. 13/301,024, which is a continuation-in-part of application No. 12/852,286, filed on Aug. 6, 2010, now Pat. No. 8,219,182, which is a continuation of application No. 10/990,327, filed on Nov. 16, 2004, now Pat. No. 7,792,569, which is a continuation of application No. 10/124,757, filed on Apr. 16, 2002, now Pat. No. 6,862,470, which is a continuation-in-part of application No. 09/717,909, filed on Nov. 20, 2000, now Pat. No. 6,725,083, which is a continuation-in-part of application No. 09/343,975, filed on Jun. 30, 1999, now Pat. No. 6,347,241, which is a continuation-in-part of application No. 09/241,936, filed on Feb. 2, 1999, now Pat. No. 6,161,034, application No. 13/310,024, which is a continuation-in-part of application No. 12/592,020, filed on Nov. 18, 2009, now Pat. No. 8,177,792, which is a continuation of application No. 10/174,401, filed on Jun. 17, 2002, now Pat. No. 7,651,505, application No. 13/301,024, which is a continuation-in-part of application No. 10/911,106, filed on Aug. 3, 2004, now Pat. No. 8,282,573, which is a continuation-in-part of application No. 10/642,406, filed on Aug. 15, 2003, now Pat. No. 7,819,819, which is a continuation-in-part of application No. 10/734,915, filed on Feb. 24, 2003, now Pat. No. 7,189,206.

(60) Provisional application No. 60/835,740, filed on Aug. 4, 2006.

(51) Int. Cl.
*A61B 19/00* (2006.01)
*A61K 9/00* (2006.01)
*A61B 17/00* (2006.01)

(52) U.S. Cl.
CPC ....... *A61B 19/54* (2013.01); *A61B 2017/00004* (2013.01); *A61B 2017/00831* (2013.01); *A61B 2017/00898* (2013.01); *A61B 2019/5408* (2013.01); *A61B 2019/5425* (2013.01); *A61B 2019/5462* (2013.01); *A61B 2019/5487* (2013.01); *A61K 9/0024* (2013.01)

(58) Field of Classification Search
CPC ........ A61B 10/00; A61B 10/02; A61B 10/06; A61M 5/00; A61M 5/142; A61M 31/00; A61M 31/007; A61M 2005/00; A61K 9/14; A61K 9/146; A61K 9/16; A61K 9/1652; A61K 9/20; A61K 9/2013; A61K 9/2022; A61K 9/205; A61K 9/2054; A61K 9/2059; A61K 9/2072
USPC .................................. 424/465–489, 422, 426
See application file for complete search history.

(56) References Cited

U.S. PATENT DOCUMENTS

| | | | |
|---|---|---|---|
| 2,192,270 | A | 3/1940 | McGowan |
| 2,481,408 | A | 9/1949 | Fuller et al. |

(Continued)

FOREIGN PATENT DOCUMENTS

| | | |
|---|---|---|
| DE | 1029528 B | 5/1958 |
| EP | 0146699 A1 | 7/1985 |

(Continued)

OTHER PUBLICATIONS

Sha et al (Polyethylene Glycol as a Binder for Tablets, vol. 66, No. 11, Nov. 1977, Journal of pharmaceutical Sciences).*

(Continued)

*Primary Examiner* — Michael G Hartley
*Assistant Examiner* — Micah-Paul Young

(57) ABSTRACT

A method for treating a site within a patient from which tissue has been removed includes providing at least one press-formed marker body formed of polysaccharide and a suitable binder; and placing the at least one of the press-formed marker body within the site where tissue has been removed so as to provide hemostasis therein.

12 Claims, 1 Drawing Sheet

(56) References Cited

U.S. PATENT DOCUMENTS

| | | | |
|---|---|---|---|
| 2,832,888 A | 4/1958 | Houston |
| 2,899,362 A | 8/1959 | Sieger, Jr. et al. |
| 2,907,327 A | 10/1959 | White |
| 3,005,457 A | 10/1961 | Millman |
| 3,128,744 A | 4/1964 | Jefferts et al. |
| 3,341,417 A | 9/1967 | Sinaiko |
| 3,402,712 A | 9/1968 | Eisenhand |
| 3,516,412 A | 6/1970 | Ackerman |
| 3,593,343 A | 7/1971 | Viggers |
| 3,757,781 A | 9/1973 | Smart |
| 3,818,894 A | 6/1974 | Wichterle et al. |
| 3,820,545 A | 6/1974 | Jefferts |
| 3,823,212 A | 7/1974 | Chvapil |
| 3,921,632 A | 11/1975 | Bardani |
| 4,005,699 A | 2/1977 | Bucalo |
| 4,007,732 A | 2/1977 | Kvavle et al. |
| 4,041,931 A | 8/1977 | Elliott et al. |
| 4,086,914 A | 5/1978 | Moore |
| 4,103,690 A | 8/1978 | Harris |
| 4,105,030 A | 8/1978 | Kercso |
| 4,127,774 A | 11/1978 | Gillen |
| 4,172,449 A | 10/1979 | LeRoy et al. |
| 4,197,846 A | 4/1980 | Bucalo |
| 4,217,889 A | 8/1980 | Radovan et al. |
| 4,276,885 A | 7/1981 | Tickner et al. |
| 4,294,241 A | 10/1981 | Miyata |
| 4,298,998 A | 11/1981 | Naficy |
| 4,331,654 A | 5/1982 | Morris |
| 4,347,234 A | 8/1982 | Wahlig et al. |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,549,560 A | 10/1985 | Andis |
| 4,582,061 A | 4/1986 | Fry |
| 4,582,640 A | 4/1986 | Smestad et al. |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,740,208 A | 4/1988 | Cavon |
| 4,762,128 A | 8/1988 | Rosenbluth |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Carter |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,938,763 A | 7/1990 | Dunn et al. |
| 4,950,234 A | 8/1990 | Fujioka et al. |
| 4,950,665 A | 8/1990 | Floyd |
| 4,963,150 A | 10/1990 | Brauman |
| 4,970,298 A | 11/1990 | Silver et al. |
| 4,989,608 A | 2/1991 | Ratner |
| 4,994,013 A | 2/1991 | Suthanthiran et al. |
| 4,994,028 A | 2/1991 | Leonard et al. |
| 5,012,818 A | 5/1991 | Joishy |
| 5,018,530 A | 5/1991 | Rank et al. |
| 5,035,891 A | 7/1991 | Runkel et al. |
| 5,059,197 A | 10/1991 | Urie et al. |
| 5,081,997 A | 1/1992 | Bosley, Jr. et al. |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,307 A | 9/1992 | Gluck |
| 5,147,631 A | 9/1992 | Glajch et al. |
| 5,162,430 A | 11/1992 | Rhee et al. |
| 5,163,896 A | 11/1992 | Suthanthiran et al. |
| 5,195,540 A | 3/1993 | Shiber |
| 5,197,482 A | 3/1993 | Rank et al. |
| 5,197,846 A | 3/1993 | Uno et al. |
| 5,199,441 A | 4/1993 | Hogle |
| 5,201,704 A | 4/1993 | Ray |
| 5,219,339 A | 6/1993 | Saito |
| 5,221,269 A | 6/1993 | Miller et al. |
| 5,231,615 A | 7/1993 | Endoh |
| 5,234,426 A | 8/1993 | Rank et al. |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,312,435 A | 5/1994 | Nash et al. |
| 5,320,100 A | 6/1994 | Herweck et al. |
| 5,320,613 A | 6/1994 | Houge et al. |
| 5,328,955 A | 7/1994 | Rhee et al. |
| 5,334,216 A | 8/1994 | Vidal et al. |
| 5,334,381 A | 8/1994 | Unger |
| 5,344,640 A | 9/1994 | Deutsch et al. |
| 5,353,804 A | 10/1994 | Kornberg et al. |
| 5,354,623 A | 10/1994 | Hall |
| 5,358,514 A | 10/1994 | Schulman et al. |
| 5,366,756 A | 11/1994 | Chesterfield et al. |
| 5,368,030 A | 11/1994 | Zinreich et al. |
| 5,388,588 A | 2/1995 | Nabai et al. |
| 5,394,875 A | 3/1995 | Lewis et al. |
| 5,395,319 A | 3/1995 | Hirsch et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,431,639 A | 7/1995 | Shaw |
| 5,433,204 A | 7/1995 | Olson |
| 5,449,560 A | 9/1995 | Antheunis et al. |
| 5,451,406 A | 9/1995 | Lawin et al. |
| 5,458,643 A | 10/1995 | Oka et al. |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,545,180 A | 8/1996 | Le et al. |
| 5,549,560 A | 8/1996 | Van de Wijdeven |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A * | 7/1997 | Faarup et al. ................ 514/250 |
| 5,657,366 A | 8/1997 | Nakayama |
| 5,665,092 A | 9/1997 | Mangiardi et al. |
| 5,667,767 A | 9/1997 | Greff et al. |
| 5,669,882 A | 9/1997 | Pyles |

(56) References Cited

U.S. PATENT DOCUMENTS

| | | |
|---|---|---|
| 5,673,841 A | 10/1997 | Schulze et al. |
| 5,676,146 A | 10/1997 | Scarborough |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,682 A | 12/1997 | Thompson |
| 5,702,716 A | 12/1997 | Dunn et al. |
| 5,716,981 A | 2/1998 | Hunter et al. |
| 5,747,060 A | 5/1998 | Sackler et al. |
| 5,752,974 A | 5/1998 | Rhee et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,771 A | 7/1998 | Hussman |
| 5,782,775 A | 7/1998 | Milliman et al. |
| 5,795,308 A | 8/1998 | Russin |
| 5,799,099 A | 8/1998 | Wang et al. |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A | 10/1998 | Lombardi et al. |
| 5,824,081 A | 10/1998 | Knapp et al. |
| 5,826,776 A | 10/1998 | Schulze et al. |
| 5,830,178 A | 11/1998 | Jones et al. |
| 5,830,222 A | 11/1998 | Makower |
| 5,842,477 A | 12/1998 | Naughton et al. |
| 5,842,999 A | 12/1998 | Pruitt et al. |
| 5,845,646 A | 12/1998 | Lemelson |
| 5,846,220 A | 12/1998 | Elsberry |
| 5,851,508 A | 12/1998 | Greff et al. |
| 5,853,366 A | 12/1998 | Dowlatshahi |
| 5,865,806 A | 2/1999 | Howell |
| 5,869,080 A | 2/1999 | McGregor et al. |
| 5,871,501 A | 2/1999 | Leschinsky et al. |
| 5,876,340 A | 3/1999 | Tu et al. |
| 5,879,357 A | 3/1999 | Heaton et al. |
| 5,891,558 A | 4/1999 | Bell et al. |
| 5,897,507 A | 4/1999 | Kortenbach et al. |
| 5,902,310 A | 5/1999 | Foerster et al. |
| 5,911,705 A | 6/1999 | Howell |
| 5,916,164 A | 6/1999 | Fitzpatrick et al. |
| 5,921,933 A | 7/1999 | Sarkis et al. |
| 5,922,024 A | 7/1999 | Janzen et al. |
| 5,928,626 A | 7/1999 | Klaveness et al. |
| 5,928,773 A | 7/1999 | Andersen |
| 5,941,439 A | 8/1999 | Kammerer et al. |
| 5,941,890 A | 8/1999 | Voegele et al. |
| 5,942,209 A | 8/1999 | Leavitt et al. |
| 5,948,425 A | 9/1999 | Janzen et al. |
| 5,954,670 A | 9/1999 | Baker |
| 5,972,817 A | 10/1999 | Haines et al. |
| 5,976,146 A | 11/1999 | Ogawa et al. |
| 5,980,564 A | 11/1999 | Stinson |
| 5,989,265 A | 11/1999 | Bouquet De La Joliniere et al. |
| 6,015,541 A | 1/2000 | Greff et al. |
| 6,030,333 A | 2/2000 | Sioshansi et al. |
| 6,053,925 A | 4/2000 | Barnhart |
| 6,056,700 A | 5/2000 | Burney et al. |
| 6,066,122 A | 5/2000 | Fisher |
| 6,066,325 A | 5/2000 | Wallace et al. |
| 6,071,301 A | 6/2000 | Cragg et al. |
| 6,071,310 A | 6/2000 | Picha et al. |
| 6,071,496 A | 6/2000 | Stein et al. |
| 6,090,996 A | 7/2000 | Li |
| 6,096,065 A | 8/2000 | Crowley |
| 6,096,070 A | 8/2000 | Ragheb et al. |
| 6,106,473 A | 8/2000 | Violante et al. |
| 6,117,108 A | 9/2000 | Woehr et al. |
| 6,120,536 A | 9/2000 | Ding et al. |
| 6,135,993 A | 10/2000 | Hussman |
| 6,142,955 A | 11/2000 | Farascioni et al. |
| 6,159,240 A | 12/2000 | Sparer et al. |
| 6,159,445 A | 12/2000 | Klaveness et al. |
| 6,161,034 A | 12/2000 | Burbank et al. |
| 6,162,192 A | 12/2000 | Cragg et al. |
| 6,166,079 A * | 12/2000 | Follen et al. ............... 514/564 |
| 6,173,715 B1 | 1/2001 | Sinanan et al. |
| 6,174,330 B1 | 1/2001 | Stinson |
| 6,177,062 B1 | 1/2001 | Stein et al. |
| 6,181,960 B1 | 1/2001 | Jensen et al. |
| 6,183,497 B1 | 2/2001 | Sing et al. |
| 6,190,350 B1 | 2/2001 | Davis et al. |
| 6,190,353 B1 | 2/2001 | Makower et al. |
| 6,200,258 B1 | 3/2001 | Slater et al. |
| 6,203,524 B1 | 3/2001 | Burney et al. |
| 6,203,568 B1 | 3/2001 | Lombardi et al. |
| 6,213,957 B1 | 4/2001 | Milliman et al. |
| 6,214,045 B1 | 4/2001 | Corbitt, Jr. et al. |
| 6,214,315 B1 | 4/2001 | Greff et al. |
| 6,220,248 B1 | 4/2001 | Voegele et al. |
| 6,224,630 B1 | 5/2001 | Bao et al. |
| 6,228,049 B1 | 5/2001 | Schroeder et al. |
| 6,228,055 B1 | 5/2001 | Foerster et al. |
| 6,231,615 B1 | 5/2001 | Preissman |
| 6,234,177 B1 | 5/2001 | Barsch |
| 6,241,687 B1 | 6/2001 | Voegele et al. |
| 6,241,734 B1 | 6/2001 | Scribner et al. |
| 6,251,135 B1 | 6/2001 | Stinson et al. |
| 6,251,418 B1 | 6/2001 | Ahern et al. |
| 6,261,243 B1 | 7/2001 | Burney et al. |
| 6,261,302 B1 | 7/2001 | Voegele et al. |
| 6,264,917 B1 | 7/2001 | Klaveness et al. |
| 6,270,464 B1 | 8/2001 | Fulton, III et al. |
| 6,270,472 B1 | 8/2001 | Antaki et al. |
| 6,287,278 B1 | 9/2001 | Woehr et al. |
| 6,287,332 B1 | 9/2001 | Bolz et al. |
| 6,289,229 B1 | 9/2001 | Crowley |
| 6,306,154 B1 | 10/2001 | Hudson et al. |
| 6,312,429 B1 | 11/2001 | Burbank et al. |
| 6,316,522 B1 | 11/2001 | Loomis et al. |
| 6,325,789 B1 | 12/2001 | Janzen et al. |
| 6,335,029 B1 | 1/2002 | Kamath et al. |
| 6,336,904 B1 | 1/2002 | Nikolchev |
| 6,340,367 B1 | 1/2002 | Stinson et al. |
| 6,343,227 B1 | 1/2002 | Crowley |
| 6,347,240 B1 | 2/2002 | Foley et al. |
| 6,347,241 B2 | 2/2002 | Burbank et al. |
| 6,350,244 B1 * | 2/2002 | Fisher ............... 600/562 |
| 6,350,274 B1 | 2/2002 | Li |
| 6,354,989 B1 | 3/2002 | Nudeshima |
| 6,356,112 B1 | 3/2002 | Tran et al. |
| 6,356,782 B1 | 3/2002 | Sirimanne et al. |
| 6,358,217 B1 | 3/2002 | Bourassa |
| 6,363,940 B1 | 4/2002 | Krag |
| 6,371,904 B1 | 4/2002 | Sirimanne et al. |
| 6,394,965 B1 * | 5/2002 | Klein ............... 600/564 |
| 6,403,758 B1 | 6/2002 | Loomis |
| 6,405,733 B1 | 6/2002 | Fogarty et al. |
| 6,409,742 B1 | 6/2002 | Fulton, III et al. |
| 6,419,621 B1 | 7/2002 | Sioshansi et al. |
| 6,424,857 B1 | 7/2002 | Henrichs et al. |
| 6,425,903 B1 | 7/2002 | Voegele |
| 6,427,081 B1 | 7/2002 | Burbank et al. |
| 6,436,030 B2 | 8/2002 | Rehil |
| 6,447,524 B1 | 9/2002 | Knodel et al. |
| 6,447,527 B1 | 9/2002 | Thompson et al. |
| 6,450,937 B1 | 9/2002 | Mercereau et al. |
| 6,450,938 B1 | 9/2002 | Miller |
| 6,471,700 B1 | 10/2002 | Burbank et al. |
| 6,478,790 B2 | 11/2002 | Bardani |
| 6,506,156 B1 | 1/2003 | Jones et al. |
| 6,511,468 B1 | 1/2003 | Cragg et al. |
| 6,511,650 B1 | 1/2003 | Eiselt et al. |
| 6,537,193 B1 | 3/2003 | Lennox |
| 6,540,981 B2 | 4/2003 | Klaveness et al. |

(56) References Cited

U.S. PATENT DOCUMENTS

| | | | |
|---|---|---|---|
| 6,544,185 B2 | 4/2003 | Montegrande | |
| 6,544,231 B1 | 4/2003 | Palmer et al. | |
| 6,551,253 B2 | 4/2003 | Worm et al. | |
| 6,554,760 B2 * | 4/2003 | Lamoureux et al. | 600/7 |
| 6,562,317 B2 | 5/2003 | Greff et al. | |
| 6,564,806 B1 | 5/2003 | Fogarty et al. | |
| 6,565,551 B1 | 5/2003 | Jones et al. | |
| 6,567,689 B2 | 5/2003 | Burbank et al. | |
| 6,575,888 B2 | 6/2003 | Zamora et al. | |
| 6,575,991 B1 | 6/2003 | Chesbrough et al. | |
| 6,585,773 B1 | 7/2003 | Xie | |
| 6,605,047 B2 | 8/2003 | Zarins et al. | |
| 6,610,026 B2 | 8/2003 | Cragg et al. | |
| 6,613,002 B1 | 9/2003 | Clark et al. | |
| 6,616,630 B1 | 9/2003 | Woehr et al. | |
| 6,626,850 B1 | 9/2003 | Chau et al. | |
| 6,626,899 B2 | 9/2003 | Houser et al. | |
| 6,628,982 B1 | 9/2003 | Thomas et al. | |
| 6,629,947 B1 | 10/2003 | Sahatjian et al. | |
| 6,636,758 B2 | 10/2003 | Sanchez et al. | |
| 6,638,234 B2 | 10/2003 | Burbank et al. | |
| 6,638,308 B2 | 10/2003 | Corbitt, Jr. et al. | |
| 6,652,442 B2 | 11/2003 | Gatto | |
| 6,656,192 B2 | 12/2003 | Espositio et al. | |
| 6,659,933 B2 | 12/2003 | Asano | |
| 6,662,041 B2 | 12/2003 | Burbank et al. | |
| 6,699,205 B2 | 3/2004 | Fulton, III et al. | |
| 6,712,774 B2 | 3/2004 | Voegele et al. | |
| 6,712,836 B1 | 3/2004 | Berg et al. | |
| 6,716,444 B1 | 4/2004 | Castro et al. | |
| 6,725,083 B1 | 4/2004 | Burbank et al. | |
| 6,730,042 B2 | 5/2004 | Fulton et al. | |
| 6,730,044 B2 | 5/2004 | Stephens et al. | |
| 6,746,661 B2 | 6/2004 | Kaplan | |
| 6,746,773 B2 | 6/2004 | Llanos et al. | |
| 6,752,154 B2 | 6/2004 | Fogarty et al. | |
| 6,766,186 B1 | 7/2004 | Hoyns et al. | |
| 6,774,278 B1 | 8/2004 | Ragheb et al. | |
| 6,780,179 B2 | 8/2004 | Lee et al. | |
| 6,824,507 B2 | 11/2004 | Miller | |
| 6,824,527 B2 | 11/2004 | Gollobin | |
| 6,846,320 B2 | 1/2005 | Ashby et al. | |
| 6,862,470 B2 * | 3/2005 | Burbank et al. | 600/431 |
| 6,863,685 B2 | 3/2005 | Davila et al. | |
| 6,881,226 B2 | 4/2005 | Corbitt, Jr. et al. | |
| 6,899,731 B2 | 5/2005 | Li et al. | |
| 6,918,927 B2 | 7/2005 | Bates et al. | |
| 6,936,014 B2 | 8/2005 | Vetter et al. | |
| 6,939,318 B2 | 9/2005 | Stenzel | |
| 6,945,973 B2 | 9/2005 | Bray | |
| 6,951,564 B2 | 10/2005 | Espositio et al. | |
| 6,958,044 B2 | 10/2005 | Burbank et al. | |
| 6,992,233 B2 | 1/2006 | Drake et al. | |
| 6,994,712 B1 | 2/2006 | Fisher et al. | |
| 7,001,341 B2 | 2/2006 | Gellman et al. | |
| 7,008,382 B2 | 3/2006 | Adams et al. | |
| 7,014,610 B2 | 3/2006 | Koulik | |
| 7,025,765 B2 | 4/2006 | Balbierz et al. | |
| 7,041,047 B2 | 5/2006 | Gellman et al. | |
| 7,044,957 B2 | 5/2006 | Foerster et al. | |
| 7,083,576 B2 | 8/2006 | Zarins et al. | |
| 7,125,397 B2 | 10/2006 | Woehr et al. | |
| 7,135,978 B2 | 11/2006 | Gisselberg et al. | |
| 7,160,258 B2 | 1/2007 | Imran et al. | |
| 7,172,549 B2 | 2/2007 | Slater et al. | |
| 7,214,211 B2 | 5/2007 | Woehr et al. | |
| 7,229,417 B2 | 6/2007 | Foerster et al. | |
| 7,236,816 B2 | 6/2007 | Kumar et al. | |
| 7,264,613 B2 | 9/2007 | Woehr et al. | |
| 7,280,865 B2 | 10/2007 | Adler | |
| 7,294,118 B2 | 11/2007 | Saulenas et al. | |
| 7,297,725 B2 | 11/2007 | Winterton et al. | |
| 7,329,402 B2 | 2/2008 | Unger et al. | |
| 7,329,414 B2 | 2/2008 | Fisher et al. | |
| 7,407,054 B2 | 8/2008 | Seiler et al. | |
| 7,416,533 B2 | 8/2008 | Gellman et al. | |
| 7,424,320 B2 | 9/2008 | Chesbrough et al. | |
| 7,449,000 B2 | 11/2008 | Adams et al. | |
| 7,527,610 B2 | 5/2009 | Erickson | |
| 7,534,452 B2 | 5/2009 | Chernomorsky et al. | |
| 7,569,065 B2 | 8/2009 | Chesbrough et al. | |
| 7,577,473 B2 | 8/2009 | Davis et al. | |
| 7,637,948 B2 | 12/2009 | Corbitt, Jr. | |
| 7,651,505 B2 | 1/2010 | Lubock et al. | |
| 7,668,582 B2 | 2/2010 | Sirimanne et al. | |
| 7,670,350 B2 | 3/2010 | Selis | |
| 7,783,336 B2 | 8/2010 | Macfarlane et al. | |
| 7,792,569 B2 * | 9/2010 | Burbank et al. | 600/431 |
| 7,819,820 B2 | 10/2010 | Field et al. | |
| 7,844,319 B2 | 11/2010 | Susil et al. | |
| 7,877,133 B2 | 1/2011 | Burbank et al. | |
| 7,914,553 B2 | 3/2011 | Ferree | |
| 7,945,307 B2 | 5/2011 | Lubock et al. | |
| 7,978,825 B2 | 7/2011 | Ngo | |
| 8,011,508 B2 | 9/2011 | Seiler et al. | |
| 8,128,641 B2 | 3/2012 | Wardle | |
| 8,219,182 B2 * | 7/2012 | Burbank et al. | 600/431 |
| 8,306,602 B2 | 11/2012 | Sirimanne et al. | |
| 8,320,993 B2 | 11/2012 | Sirimanne et al. | |
| 8,320,994 B2 | 11/2012 | Sirimanne et al. | |
| 8,320,995 B2 | 11/2012 | Schwamb, Jr. | |
| 8,334,424 B2 | 12/2012 | Szypka | |
| 8,414,602 B2 | 4/2013 | Selis | |
| 8,437,834 B2 | 5/2013 | Carr et al. | |
| 8,442,623 B2 | 5/2013 | Nicoson et al. | |
| 8,454,629 B2 | 6/2013 | Selis | |
| 8,486,028 B2 | 7/2013 | Field | |
| 8,579,931 B2 | 11/2013 | Chesbrough et al. | |
| 8,626,269 B2 * | 1/2014 | Jones et al. | 600/431 |
| 8,626,270 B2 | 1/2014 | Burbank et al. | |
| 8,639,315 B2 | 1/2014 | Burbank et al. | |
| 2001/0003791 A1 | 6/2001 | Burbank et al. | |
| 2001/0006616 A1 | 7/2001 | Leavitt et al. | |
| 2001/0033867 A1 | 10/2001 | Ahern et al. | |
| 2001/0034528 A1 | 10/2001 | Foerster et al. | |
| 2001/0049481 A1 | 12/2001 | Fulton, III et al. | |
| 2002/0004060 A1 | 1/2002 | Heublein et al. | |
| 2002/0016625 A1 | 2/2002 | Falotico et al. | |
| 2002/0022883 A1 | 2/2002 | Burg | |
| 2002/0026201 A1 | 2/2002 | Foerster et al. | |
| 2002/0035324 A1 | 3/2002 | Sirimanne et al. | |
| 2002/0038087 A1 | 3/2002 | Burbank et al. | |
| 2002/0044969 A1 * | 4/2002 | Harden et al. | 424/470 |
| 2002/0045842 A1 | 4/2002 | Van Bladel et al. | |
| 2002/0052572 A1 | 5/2002 | Franco et al. | |
| 2002/0055731 A1 | 5/2002 | Atala et al. | |
| 2002/0058868 A1 | 5/2002 | Hoshino et al. | |
| 2002/0058882 A1 | 5/2002 | Fulton, III et al. | |
| 2002/0077687 A1 | 6/2002 | Ahn | |
| 2002/0082517 A1 | 6/2002 | Klein | |
| 2002/0082519 A1 | 6/2002 | Miller et al. | |
| 2002/0082682 A1 | 6/2002 | Barclay et al. | |
| 2002/0082683 A1 | 6/2002 | Stinson et al. | |
| 2002/0095204 A1 | 7/2002 | Thompson et al. | |
| 2002/0095205 A1 | 7/2002 | Edwin et al. | |
| 2002/0107437 A1 | 8/2002 | Sirimanne et al. | |
| 2002/0133148 A1 | 9/2002 | Daniel et al. | |
| 2002/0143359 A1 | 10/2002 | Fulton, III et al. | |
| 2002/0165608 A1 | 11/2002 | Llanos et al. | |
| 2002/0177776 A1 | 11/2002 | Crawford Kellar et al. | |
| 2002/0188195 A1 | 12/2002 | Mills | |
| 2002/0188196 A1 * | 12/2002 | Burbank et al. | 600/431 |
| 2002/0193815 A1 | 12/2002 | Foerster et al. | |
| 2002/0193867 A1 | 12/2002 | Gladdish, Jr. et al. | |
| 2003/0032969 A1 | 2/2003 | Gannoe et al. | |
| 2003/0036803 A1 | 2/2003 | McGhan | |
| 2003/0051735 A1 | 3/2003 | Pavcnik et al. | |
| 2003/0116806 A1 | 6/2003 | Kato | |
| 2003/0165478 A1 | 9/2003 | Sokoll | |
| 2003/0191355 A1 | 10/2003 | Ferguson | |
| 2003/0199887 A1 | 10/2003 | Ferrera et al. | |
| 2003/0225420 A1 | 12/2003 | Wardle | |
| 2003/0233101 A1 | 12/2003 | Lubock et al. | |
| 2003/0236573 A1 | 12/2003 | Evans et al. | |

(56) References Cited

U.S. PATENT DOCUMENTS

| | | |
|---|---|---|
| 2004/0001841 A1 | 1/2004 | Nagavarapu et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0068312 A1 | 4/2004 | Sigg et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0101548 A1 | 5/2004 | Pendharkar |
| 2004/0106891 A1 | 6/2004 | Langan et al. |
| 2004/0116802 A1 | 6/2004 | Jessop et al. |
| 2004/0116806 A1 | 6/2004 | Burbank et al. |
| 2004/0124105 A1 | 7/2004 | Seiler et al. |
| 2004/0127765 A1 | 7/2004 | Seiler et al. |
| 2004/0133124 A1 | 7/2004 | Bates et al. |
| 2004/0153074 A1 | 8/2004 | Bojarski et al. |
| 2004/0162574 A1 | 8/2004 | Viola |
| 2004/0167619 A1 | 8/2004 | Case et al. |
| 2004/0193044 A1 | 9/2004 | Burbank et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2004/0236211 A1 | 11/2004 | Burbank et al. |
| 2004/0236212 A1* | 11/2004 | Jones et al. .................. 600/431 |
| 2004/0236213 A1* | 11/2004 | Jones et al. .................. 600/431 |
| 2004/0253185 A1 | 12/2004 | Herweck et al. |
| 2004/0265371 A1 | 12/2004 | Looney et al. |
| 2005/0019262 A1 | 1/2005 | Chernomorsky et al. |
| 2005/0020916 A1 | 1/2005 | MacFarlane et al. |
| 2005/0033157 A1 | 2/2005 | Klein et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0063908 A1 | 3/2005 | Burbank et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1 | 4/2005 | Sirimanne et al. |
| 2005/0085724 A1 | 4/2005 | Sirimanne et al. |
| 2005/0100580 A1 | 5/2005 | Osborne et al. |
| 2005/0112151 A1 | 5/2005 | Horng |
| 2005/0113659 A1 | 5/2005 | Pothier et al. |
| 2005/0119562 A1 | 6/2005 | Jones et al. |
| 2005/0142161 A1 | 6/2005 | Freeman et al. |
| 2005/0143650 A1 | 6/2005 | Winkel |
| 2005/0143656 A1 | 6/2005 | Burbank et al. |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0208122 A1 | 9/2005 | Allen et al. |
| 2005/0216018 A1 | 9/2005 | Sennett |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0025677 A1 | 2/2006 | Verard et al. |
| 2006/0036158 A1 | 2/2006 | Field et al. |
| 2006/0036159 A1 | 2/2006 | Sirimanne et al. |
| 2006/0036165 A1 | 2/2006 | Burbank et al. |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2006/0241411 A1 | 10/2006 | Field et al. |
| 2006/0292690 A1 | 12/2006 | Liu et al. |
| 2007/0021642 A1 | 1/2007 | Lamoureux et al. |
| 2007/0038145 A1 | 2/2007 | Field |
| 2007/0057794 A1 | 3/2007 | Gisselberg et al. |
| 2007/0083132 A1 | 4/2007 | Sharrow |
| 2007/0087026 A1 | 4/2007 | Field |
| 2007/0106152 A1 | 5/2007 | Kantrowitz et al. |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0276492 A1 | 11/2007 | Andrews et al. |
| 2007/0287933 A1 | 12/2007 | Phan et al. |
| 2008/0039819 A1 | 2/2008 | Jones et al. |
| 2008/0091120 A1 | 4/2008 | Fisher |
| 2008/0097199 A1 | 4/2008 | Mullen |
| 2008/0121242 A1 | 5/2008 | Revie et al. |
| 2008/0188768 A1 | 8/2008 | Zarins et al. |
| 2008/0249436 A1 | 10/2008 | Darr |
| 2008/0269638 A1 | 10/2008 | Cooke et al. |
| 2008/0294039 A1 | 11/2008 | Jones et al. |
| 2009/0000629 A1 | 1/2009 | Hornscheidt et al. |
| 2009/0024225 A1 | 1/2009 | Stubbs |
| 2009/0030309 A1 | 1/2009 | Jones et al. |
| 2009/0069713 A1 | 3/2009 | Adams et al. |
| 2009/0076484 A1 | 3/2009 | Fukaya |
| 2009/0131825 A1 | 5/2009 | Burbank et al. |
| 2009/0171198 A1 | 7/2009 | Jones et al. |
| 2010/0010341 A1 | 1/2010 | Talpade et al. |
| 2010/0030072 A1 | 2/2010 | Casanova et al. |
| 2010/0030149 A1 | 2/2010 | Carr, Jr. |
| 2010/0042041 A1 | 2/2010 | Tune et al. |
| 2010/0082102 A1 | 4/2010 | Govil et al. |
| 2010/0204570 A1 | 8/2010 | Lubock |
| 2010/0298696 A1 | 11/2010 | Field et al. |
| 2010/0331668 A1 | 12/2010 | Ranpura |
| 2011/0028836 A1 | 2/2011 | Ranpura |
| 2011/0184280 A1 | 7/2011 | Jones et al. |
| 2011/0184449 A1 | 7/2011 | Lubock et al. |
| 2012/0078086 A1 | 3/2012 | Hoffa |
| 2012/0078087 A1 | 3/2012 | Curry |
| 2012/0078092 A1 | 3/2012 | Jones et al. |
| 2012/0179251 A1 | 7/2012 | Corbitt, Jr. |
| 2012/0215230 A1 | 8/2012 | Lubock et al. |
| 2012/0277859 A1 | 11/2012 | Govil et al. |
| 2013/0144157 A1 | 6/2013 | Jones et al. |
| 2013/0184562 A1 | 7/2013 | Talpade et al. |
| 2013/0190616 A1 | 7/2013 | Casanova et al. |
| 2013/0281847 A1 | 10/2013 | Jones et al. |
| 2013/0310686 A1 | 11/2013 | Jones et al. |
| 2014/0058258 A1 | 2/2014 | Chesbrough et al. |
| 2014/0094698 A1 | 4/2014 | Burbank et al. |
| 2014/0114186 A1 | 4/2014 | Burbank et al. |
| 2014/0142696 A1 | 5/2014 | Corbitt, Jr. |
| 2014/0194892 A1 | 7/2014 | Ranpura et al. |
| 2014/0243675 A1 | 8/2014 | Burbank et al. |
| 2015/0051477 A1 | 2/2015 | Jones et al. |

FOREIGN PATENT DOCUMENTS

| | | |
|---|---|---|
| EP | 0255123 A2 | 2/1988 |
| EP | 0292936 A2 | 11/1988 |
| EP | 0386936 A1 | 9/1990 |
| EP | 0458745 A1 | 11/1991 |
| EP | 0475077 A2 | 3/1992 |
| EP | 0481685 A1 | 4/1992 |
| EP | 0552924 A1 | 7/1993 |
| EP | 0769281 A2 | 4/1997 |
| EP | 1114618 A2 | 7/2001 |
| EP | 1163888 A1 | 12/2001 |
| EP | 1216721 A2 | 6/2002 |
| EP | 1281416 A2 | 6/2002 |
| EP | 1364628 A1 | 11/2003 |
| EP | 1493451 A1 | 1/2005 |

(56) References Cited

FOREIGN PATENT DOCUMENTS

| | | |
|---|---|---|
| EP | 1767167 A2 | 3/2007 |
| FR | 2646674 A3 | 11/1990 |
| FR | 2853521 A1 | 10/2004 |
| GB | 708148 | 4/1954 |
| JP | 2131757 A | 5/1990 |
| JP | 2006516468 A | 7/2006 |
| JP | 2007537017 A | 12/2007 |
| WO | 8906978 A1 | 8/1989 |
| WO | 9112823 A1 | 9/1991 |
| WO | 9314712 A1 | 8/1993 |
| WO | 9317671 A1 | 9/1993 |
| WO | 9317718 A1 | 9/1993 |
| WO | 9416647 A1 | 8/1994 |
| WO | 9507057 A1 | 3/1995 |
| WO | 9608208 A1 | 3/1996 |
| WO | 9806346 A1 | 2/1998 |
| WO | 9908607 A1 | 2/1999 |
| WO | 9930764 A1 | 6/1999 |
| WO | 9935966 A1 | 7/1999 |
| WO | 9951143 A1 | 10/1999 |
| WO | 0023124 A1 | 4/2000 |
| WO | 0024332 A1 | 5/2000 |
| WO | 0028554 A1 | 5/2000 |
| WO | 0038779 A1 | 7/2000 |
| WO | 0054689 A1 | 9/2000 |
| WO | 0108578 A1 | 2/2001 |
| WO | WO 0108578 A1 * | 2/2001 |
| WO | 0170114 A1 | 9/2001 |
| WO | 0207786 A2 | 1/2002 |
| WO | 03000308 A1 | 1/2003 |
| WO | 2004045444 A2 | 6/2004 |
| WO | 2004105626 A2 | 12/2004 |
| WO | 2005013832 A1 | 2/2005 |
| WO | 2005039446 A1 | 5/2005 |
| WO | 2005089664 A1 | 9/2005 |
| WO | 2005112787 A2 | 12/2005 |
| WO | 2006012630 A2 | 2/2006 |
| WO | 2006056739 A2 | 6/2006 |
| WO | 2006097331 A2 | 9/2006 |
| WO | 2006105353 A2 | 10/2006 |
| WO | 2007067255 A1 | 6/2007 |
| WO | 2007069105 A2 | 6/2007 |
| WO | 2008019001 A2 | 2/2008 |
| WO | 2008077081 A2 | 6/2008 |

OTHER PUBLICATIONS

Armstong, J.S., et al., "Differential marking of Excision Planes in Screened Breast lesions by Organically Coloured Gelatins", Journal of Clinical Pathology, Jul. 1990, No. 43 (7) pp. 604-607, XP000971447 abstract; tables 1,2.

Fucci, V., et al., "Large Bowel Transit Times Using Radioopaque Markers in Normal Cats", J. of Am. Animal Hospital Assn., Nov.-Dec. 1995 31 (6) 473-477.

Schindlbeck, N. E., et al., "Measurement of Colon Transit Time", J. of Gastroenterology, No. 28, pp. 399-404, 1990.

Shiga, et al., Preparation of Poly(D, L-lactide) and Copoly(lactide-glycolide) Microspheres of Uniform Size, J. Pharm. Pharmacol. 1996 48:891-895.

Eiselt, P. et al, "Development of Technologies Aiding Large—Tissue Engineering", Biotechnol. Prog., vol. 14, No. 1, pp. 134-140, 1998.

Meuris, Bart, "Calcification of Aortic Wall Tissue in Prosthetic Heart Valves: Initiation, Influencing Factors and Strategies Towards Prevention", Thesis, 2007, pp. 21-36, Leuven University Press; Leuven, Belgium.

Jong-Won Rhie, et al. "Implantation of Cultured Preadipocyte Using Chitosan/Alginate Sponge", Key Engineering Materials, Jul. 1, 2007, pp. 346-352, XP008159356, ISSN: 0252-1059, DOI: 10.4028/www.scientific.net/KEM.342-343.349, Department of Plastic Surgery, College of Medicine, The Catholic University of Korea, Seoul Korea.

Fajardo, Laurie, et al., "Placement of Endovascular Embolization Microcoils to Localize the Site of Breast Lesions Removed at Stereotactic Core Biopsy", Radiology, Jan. 1998, pp. 275-278, vol. 206—No. 1.

H. J. Gent, M.D., et al., Stereotaxic Needle Localization and Cytological Diagnosis of Occult Breast Lesions, Annals of Surgery, Nov. 1986, pp. 580-584, vol. 204—No. 5.

Press release for Biopsys Ethicon Endo-Surgery (Europe) GmbH; The Mammotome Vacuum Biopsy System. From: http://www.medicine-news.com/articles/devices/mammotome.html. 3 pages.

Johnson & Johnson: Breast Biopsy (minimally invasive): Surgical Technique: Steps in the Mamotome Surgical Procedure. From http://www.jnjgateway.com. 3 pages.

Johnson & Johnson: New Minimally Invasive Breast Biopsy Device Receives Marketing Clearance in Canada; Aug. 6, 1999. From http://www.jnjgateway.com. 4 pages.

Johnson & Johnson: Mammotome Hand Held Receives FDA Marketing Clearance for Minimally Invasive Breast Biopises; Sep. 1, 1999. From From http://www.jnjgateway.com. 5 pages.

Johnson & Johnson: The Mammotome Breast Biopsy System. From: http://www.breastcareinfo.com/aboutm.htm. 6 pages.

Cook Incorporated: Emoblization and Occlusion. From: www.cookgroup.com 6 pages.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

International Search Report for PCT/US2009/000945 mailed Jul. 16, 2009.

Written Opinion of the International Searching Authority for PCT/US2009/000945 mailed Jul. 16, 2009.

International Search Report for PCT/US2007/016902 mailed Feb. 28, 2008.

International Search Report for PCT/US2007/016902 mailed Feb. 4, 2009.

Written Opinion of the International Searching Authority for PCT/US2007/016902 mailed Feb. 4, 2009.

International Search Report for PCT/US2007016918 mailed Nov. 26, 2007.

Written Opinion of the International Searching Authority for PCT/US2007016918 mailed Feb. 4, 2009.

Collagen—Definitions from Dictionary. com.

Fibrous—Definitions from Dictionary.com.

Crook, et al. (Prostate Motion During Standard Radiotherapy as Assessed by Fiducial Markers, 1995, Radiotherapy and Oncology 37:35-42.).

Hyeong-Ho, et al. (Preparation of Macroporous Hydroxyapatite/Chitosan-Alginate Composite Scaffolds for Bone Implants, 2007, Trans Tech Publications).

Madihally, et al. (Porous chitosan scaffolds for tissue engineering, 1998, Elsevier Science Ltd.).

Zmora, et al. (Tailoring the pore architecture in 3-D alginate scaffolds by controlling the freezing regime during fabrication, 2001, Elsevier Science Ltd.).

* cited by examiner

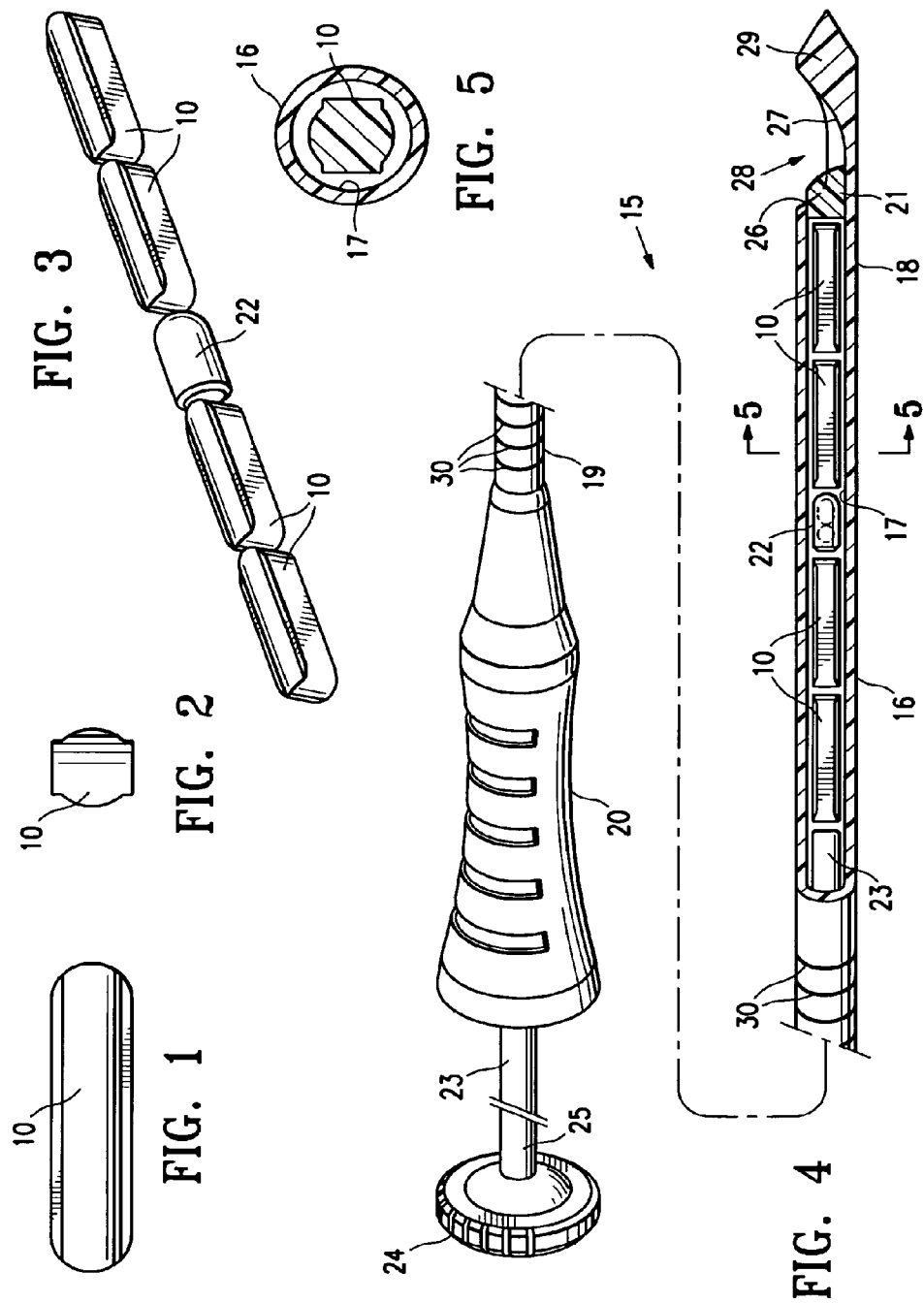

DEPLOYMENT OF POLYSACCHARIDE MARKERS FOR TREATING A SITE WITHIN A PATIENT

CROSS REFERENCE TO RELATED APPLICATIONS

This application is a continuation-in-part of U.S. patent application Ser. No. 12/070,786, entitled "DEPLOYMENT OF POLYSACCHARIDE MARKERS", filed Feb. 21, 2008, which is a continuation-in-part of U.S. patent application Ser. No. 11/881,264, filed Jul. 26, 2007, which is related to and claims priority from provisional application Ser. No. 60/835,740, filed on Aug. 4, 2006.

Also, this application is a continuation-in-part of U.S. patent application Ser. No. 13/155,628 entitled "FIBROUS MARKER AND INTRACORPOREAL DELIVERY THEREOF", filed Jun. 8, 2011, now U.S. Pat. No. 8,626,269, which is a continuation of U.S. patent application Ser. No. 10/444,770, filed May 23, 2003, now U.S. Pat. No. 7,983,734 B2.

Also, this application is a continuation-in-part of U.S. patent application Ser. No. 13/037,971 entitled "MARKER DELIVERY DEVICE WITH RELEASABLE PLUG", filed Mar. 1, 2011, now U.S. Pat. No. 8,361,082, which is a continuation-in-part of U.S. patent application Ser. No. 10/753,694, filed Jan. 7, 2004, now abandoned, which is a continuation-in-part of U.S. patent application Ser. No. 10/444,770, filed May 23, 2003, now U.S. Pat. No. 7,983,734 B2.

Also, this application is a continuation-in-part of U.S. patent application Ser. No. 12/852,286 entitled CAVITY-FILLING BIOPSY SITE MARKERS, filed Aug. 6, 2010, now U.S. Pat. No. 8,219,182, which is a continuation of U.S. patent application Ser. No. 10/990,327, filed Nov. 16, 2004, now U.S. Pat. No. 7,792,569, which is a continuation of U.S. patent application Ser. No. 10/124,757, filed Apr. 16, 2002, now U.S. Pat. No. 6,862,470, which is a continuation-in-part of U.S. patent application Ser. No. 09/717,909, filed Nov. 20, 2000, now U.S. Pat. No. 6,725,083, which is a continuation-in-part of U.S. patent application Ser. No. 09/343,975, filed Jun. 30, 1999, now U.S. Pat. No. 6,347,241, which is a continuation-in-part of U.S. patent application Ser. No. 09/241,936, filed Feb. 2, 1999, now U.S. Pat. No. 6,161,034.

Also, this application is a continuation-in-part of U.S. patent application Ser. No. 12/592,020 entitled PLUGGED TIP DELIVERY TUBE FOR MARKER PLACEMENT, filed Nov. 18, 2009, now U.S. Pat. No. 8,177,792, which is a continuation of U.S. patent application Ser. No. 10/174,401, filed Jun. 17, 2002, now U.S. Pat. No. 7,651,505.

Also, this application is a continuation-in-part of U.S. patent application Ser. No. 10/911,106 entitled BIOPSY DEVICE WITH SELECTABLE TISSUE RECEIVING APERTURE ORIENTATION AND SITE ILLUMINATION, filed Aug. 3, 2004, now U.S. Pat. No. 8,282,573, which is a continuation-in-part of U.S. patent application Ser. No. 10/642,406, filed Aug. 15, 2003, now U.S. Pat. No. 7,819,819, which is a continuation-in-part of U.S. patent application Ser. No. 10/374,915, filed Feb. 24, 2003, now U.S. Pat. No. 7,189,206.

FIELD OF THE INVENTION

The invention is generally directed to remotely detectable, intracorporeal markers and devices and methods for the delivery of such markers to a desired location within a patient's body.

BACKGROUND OF THE INVENTION

In diagnosing and treating certain medical conditions, it is often desirable to mark a suspicious body site for the subsequent taking of a biopsy specimen, for delivery of medicine, radiation, or other treatment, for the relocation of a site from which a biopsy specimen was taken, or at which some other procedure was performed. As is known, obtaining a tissue sample by biopsy and the subsequent examination are typically employed in the diagnosis of cancers and other malignant tumors, or to confirm that a suspected lesion or tumor is not malignant. The information obtained from these diagnostic tests and/or examinations is frequently used to devise a therapeutic plan for the appropriate surgical procedure or other course of treatment.

In many instances, the suspicious tissue to be sampled is located in a subcutaneous site, such as inside a human breast. To minimize surgical intrusion into a patient's body, it is often desirable to insert a small instrument, such as a biopsy needle, into the body for extracting the biopsy specimen while imaging the procedure using fluoroscopy, ultrasonic imaging, x-rays, magnetic resonance imaging (MRI) or any other suitable form of imaging technique or palpation. Examination of tissue samples taken by biopsy is of particular significance in the diagnosis and treatment of breast cancer. In the ensuing discussion, the biopsy and treatment site described will generally be the human breast, although the invention is suitable for marking biopsy sites in other parts of the human and other mammalian body as well.

Periodic physical examination of the breasts and mammography are important for early detection of potentially cancerous lesions. In mammography, the breast is compressed between two plates while specialized x-ray images are taken. If an abnormal mass in the breast is found by physical examination or mammography, ultrasound may be used to determine whether the mass is a solid tumor or a fluid-filled cyst. Solid masses are usually subjected to some type of tissue biopsy to determine if the mass is cancerous.

If a solid mass or lesion is large enough to be palpable, a tissue specimen can be removed from the mass by a variety of techniques, including but not limited to open surgical biopsy, a technique known as Fine Needle Aspiration Biopsy (FNAB) and instruments characterized as "vacuum assisted large core biopsy devices".

If a solid mass of the breast is small and non-palpable (e.g., the type typically discovered through mammography), a vacuum assisted large core biopsy procedure is usually used. In performing a stereotactic biopsy of a breast, the patient lies on a special biopsy table with her breast compressed between the plates of a mammography apparatus and two separate x-rays or digital video views are taken from two different points of view. A computer calculates the exact position of the lesion as well as depth of the lesion within the breast. Thereafter, a mechanical stereotactic apparatus is programmed with the coordinates and depth information is calculated by the computer, and such apparatus is used to precisely advance the biopsy needle into the small lesion. The stereotactic technique may be used to obtain histologic specimens. Usually at least five separate biopsy specimens are obtained from locations around the small lesion as well as one from the center of the lesion.

The available treatment options for cancerous lesions of the breast include various degrees of mastectomy or lumpectomy, radiation therapy, chemotherapy and combinations of these treatments. However, radiographically visible tissue features, originally observed in a mammogram, may be removed, altered or obscured by the biopsy procedure, and may heal or otherwise become altered following the biopsy. In order for the surgeon or radiation oncologist to direct surgical or radiation treatment to the precise location of the breast lesion several days or weeks after the biopsy procedure was performed, it is desirable that a biopsy site marker be placed in the patient's body to serve as a landmark for subsequent location of the lesion site. A biopsy site marker may be a permanent marker (e.g., a metal marker visible under x-ray examination), or a temporary marker (e.g., a bioresorbable marker detectable with ultrasound). While current radiographic type markers may persist at the biopsy site, an additional mammography generally must be performed at the time of follow up treatment or surgery in order to locate the site of the previous surgery or biopsy. In addition, once the site of the previous procedure is located using mammography, the site must usually be marked with a location wire which has a hook on the end which is advanced into site of the previous procedure. The hook is meant to fix the tip of the location wire with respect to the site of the previous procedure so that the patient can then be removed from the confinement of the mammography apparatus and the follow-up procedure performed. However, as the patient is removed from the mammography apparatus, or otherwise transported the position of the location wire can change or shift in relation to the site of the previous procedure. This, in turn, can result in follow-up treatments being misdirected to an undesired portion of the patient's tissue.

As an alternative or adjunct to radiographic imaging, ultrasonic imaging (herein abbreviated as "USI") or visualization techniques can be used to image the tissue of interest at the site of interest during a surgical or biopsy procedure or follow-up procedure. USI is capable of providing precise location and imaging of suspicious tissue, surrounding tissue and biopsy instruments within the patient's body during a procedure. Such imaging facilitates accurate and controllable removal or sampling of the suspicious tissue so as to minimize trauma to surrounding healthy tissue.

For example, during a breast biopsy procedure, the biopsy device is often imaged with USI while the device is being inserted into the patient's breast and activated to remove a sample of suspicious breast tissue. As USI is often used to image tissue during follow-up treatment, it may be desirable to have a marker, similar to the radiographic markers discussed above, which can be placed in a patient's body at the site of a surgical procedure and which are visible using USI. Such a marker enables a follow-up procedure to be performed without the need for traditional radiographic mammography imaging which, as discussed above, can be subject to inaccuracies as a result of shifting of the location wire as well as being tedious and uncomfortable for the patient.

Placement of a marker or multiple markers at a location within a patient's body requires delivery devices capable of holding markers within the device until the device is properly situated within a breast or other body location. Accordingly, devices and methods for retaining markers within a marker delivery device while allowing their expulsion from the devices at desired intracorporeal locations are desired.

In addition to marking functions, frequently it is desirable to provide treatments with the marker members such as hemostatic treatment and the like.

SUMMARY OF THE INVENTION

The invention is generally directed to a remotely imageable marker system suitable for deployment at a site within a patient's body, particularly a biopsy site such as in a patient's breast. The imageable marker system has a plurality of marker members containing polysaccharide in sufficient amounts to provide hemostatic properties and has a molecular weight of about 3500 to about 200,000 Daltons. The polysaccharide containing marker members are preferably press-formed from a dry powder into a pellet shape. The polysaccharide and binder powder should have a particle size of about 10 to about 200 micrometers. The polysaccharide markers rapidly absorb body fluid and hydrate and in the process dehydrate blood at the site of deployment to rapidly initiate clotting.

The polysaccharide is preferably starch (corn starch or potato starch) but a variety of bioabsorbable polysaccharides are suitable, including glycogen, cellulose, chitin, chitosan, dextran, pectins, glucans, agar, alginate and carrageen. The binder is preferably methylcellulose but a variety of binders may be employed in lieu of or in addition to methylcellulose. Other suitable binders include hydroxyethyl cellulose, polyethylene glycol, polyvinyl alcohol, polyvinylpyrolidone.

The remotely imageable marker system preferably includes a marker body with a radiopaque element connected thereto or incorporated therein to provide long term identification of the intracorporeal site. Preferably, the radiopaque element is formed of non-magnetic material to avoid interference with magnetic resonance imaging (MRI). Suitable non-magnetic materials include titanium, platinum, gold, iridium, tantalum, tungsten, silver, rhodium, non-magnetic stainless steel (316) and the like. The radiopaque element should have a shape that is readily recognized at the intracorporeal site when remotely imaged. The radiopaque element should have a maximum dimension of about 0.5 to about 5 mm, preferably about 1 to about 3 mm to ensure remote identification, particularly with MRI. The marker body having a radiopaque element is preferably formed of a bioabsorbable polymeric material such as polylactic-polyglycolic acid (polylactide-co-glycolide) with a longer dissolution time than the polysaccharide pellets, although the latter may be used.

The polysaccharide containing pellets will generally have a transverse dimension of about 0.02 to about 0.1 inch (0.5-2.5 mm), preferably about 0.035 to about 0.075 inch (0.9-1.9 mm), and typically about 0.056 inch (1.4 mm) The pellets will have a length of about 0.1 to about 0.4 inch (2.5-10 mm), preferably about 0.15 to about 0.35 inch (3.8-8.9 mm) The pellets provide sufficient column strength to facilitate introduction into and discharge thereof from the tubular delivery device. The markers are preferably arranged for delivery within the delivery tube with the marker having a radiopaque element between two adjacent marker members formed of polysaccharide. As presently contemplated, within the delivery tube there will be two polysaccharide marker members distal and two polysaccharide marker members proximal to the marker having a radiopaque element.

The marker member embodying features of the invention can be readily delivered to the desired location by suitable delivery systems such as disclosed in application Ser. No. 10/444,770, filed on May 23, 2003, now U.S. Pat. No. 7,983,734 B2, and Ser. No. 10/753,694, filed Jan. 7, 2004. The marker delivery system generally has an elongated cannula or tube with proximal and distal ports and an inner lumen extending between the ports. The marker member is slidably disposed within the inner lumen of the delivery cannula and a plunger slidably disposed within the inner lumen of the delivery cannula proximal to the markers. The plunger is movable from an initial position proximal to the markers within the tube, to a delivery position close to the discharge opening in the distal end of the cannula to push the marker members out of the discharge opening into the target tissue site.

Upon being discharged into the intracorporeal target site, the plurality of polysaccharide containing markers quickly take up body fluid at the site, initiating the clotting process and providing hemostasis. The other marker member with a radiopaque marker element enables short term detection (at least three weeks, preferably at least four weeks but less than a year) by remote USI and preferably long term detection by remote mammographic imaging or MRI identification by the radiopaque element. Typically, the polysaccharide bodies dissolve in situ in about five seconds to about 2 minutes and enzymatically degrade in about 2-5 days.

The cannula of the marker delivery device may be configured to fit within the guide cannula of a biopsy device, such as a Mammotome® (sold by Johnson & Johnson), the SenoCor 360™ biopsy device sold by SenoRx (the present assignee), the EnCor™ biopsy device sold by SenoRx and or a coaxial needle guide. The delivery cannula can also be configured to fit into the proximal end of a tubular cutting element such as found in the EnCor™ biopsy system sold by SenoRx which is the subject of co-pending application Ser. No. 10/911,106, filed on Aug. 3, 2004.

One suitable delivery system suitable for delivery through a tubular cutter (e.g. as with the Encor™ system) is a syringe-type delivery system described in co-pending application Ser. No. 10/911,106, filed on Aug. 3, 2004 having a tubular shaft with a flared guide on or integral with the distal tip to facilitate engagement with the proximal end of the tubular cutter. Another syringe-type delivery system has a plugged distal tip to prevent body fluids from engaging one or more markers which may be in the tubular shaft of the delivery system. Such fluid infusions can retard or restrict discharging the markers within the inner lumen of the delivery cannula by causing the markers to take up water or swell within the lumen of the delivery cannula. Delivery systems with plugged tips are described in co-pending application Ser. No. 10/444,770, filed on May 23, 2003, now U.S. Pat. No. 7,983,734 B2, and Ser. No. 10/753,694, filed Jan. 7, 2004, which are incorporated herein in their entireties. The plugged tip type delivery systems can have a side opening for marker deployment or a plugged needle-type distal tip both of which are disclosed in the above application Ser. No. 10/753,694.

A variety of therapeutic or diagnostic agents may also be incorporated into the marker bodies. Incorporated agents can include for example, anesthetic agents to control pain, chemotherapeutic agents for treating residual neoplastic tissue or coloring agents to facilitate subsequent visual location of the site. Antibiotics, antifungal agents and antiviral agents may also be incorporated into the marker bodies.

Upon delivery to the intracorporeal site, the markers are easily identifiable from surrounding tissue at the site by ultrasonic imaging (USI).

The polysaccharide containing markers embodying features of the present invention provide several advantages. The polysaccharide marker bodies quickly dissolve in the body fluids at the site to provide to provide rapid hemostasis therein even with serious bleeding. Moreover, the materials rapidly degrade so there is no long term irritation or inflammation at the site.

Thus, the invention, in one form thereof, is directed to a method for treating a site within a patient from which tissue has been removed, including providing at least one press-formed marker body formed of polysaccharide and a suitable binder; and placing the at least one of the press-formed marker body within the site where tissue has been removed so as to provide hemostasis therein.

The invention in another form is directed to a method for treating a site within a patient from which tissue has been removed, including providing at least one unitary marker pellet formed of polysaccharide powder and a suitable binder pressed into a desired shape; and placing each individual unitary marker pellet formed of polysaccharide powder within the site where tissue has been removed so as to provide hemostasis therein.

The invention in another form is directed to a method to facilitate treating a site within a patient from which tissue has been removed, including providing a plurality of marker members, each marker member of the plurality of marker members comprising a bioabsorbable polysaccharide and a binder, the bioabsorbable polysaccharide being in sufficient amounts to exhibit hemostatic properties, the plurality of marker members being disposed within an inner lumen of a tubular delivery member; and placing the plurality of marker members in a lumen of a delivery tube configured to deliver the plurality of marker members into the site within the patient from which the tissue has been removed.

These and other advantages of the invention will become more apparent from the following detailed description of embodiments when taken in conjunction with the accompanying exemplary drawings.

BRIEF DESCRIPTION OF THE DRAWINGS

FIG. 1 is a plan view of a press-formed marker member embodying features of the invention.

FIG. 2 is an end view of the marker member shown in FIG. 1.

FIG. 3 is a perspective view of a plurality of markers arranged as they would be within a delivery tube (not shown).

FIG. 4 is a partly cut-away perspective view of a marker delivery assembly having a plurality of marker members embodying features of the invention.

FIG. 5 is a transverse cross-sectional view taken along the lines 5-5 shown in FIG. 4.

DETAILED DESCRIPTION OF THE INVENTION

FIGS. 1 and 2 illustrate a press-formed marker member 10 embodying features of the invention which is formed of a mixture of polysaccharide powder and methylcellulose powder. The press-formed marker member 10 has sufficient polysaccharide powder so as to quickly form thrombus when coming into contact with blood at an intracorporeal site. Typically, the marker member 10 will have 65% (by wt.) polysaccharide and 35% (by wt.) methylcellulose. The marker member 10 is preferably formed by mixing polysaccharide powder (corn starch or potato starch) and methylcellulose powder in appropriate amounts, placing the mixed powder in a pellet die and subjecting the powder within the pellet die to a pressure of about 6 to 40 ksi, typically about 12 ksi.

One suitable polysaccharide material is U.S.P. Topical Starch. Alternatively, Hemaderm™, which is available from Medafor, Inc. located in Minneapolis, Minn., may also be used. This product is described at least in part in U.S. Pat. No. 6,060,461.

The marker member 10 may be formed in a variety of shapes and sizes, but generally the length of the marker member is at least twice, preferably five times that of the maximum transverse dimension. The marker member 10 should have sufficient column strength to allow it to be pushed within the delivery tube without significant damage. In some instances the marker member may be partially or completely coated with a bioabsorbable polymeric material such as polylactic acid, polyglycolic acid and copolymers thereof to control the dissolution of the material of the marker member.

One suitable marker delivery system 15 is depicted in FIGS. 4 and 5 which includes a delivery tube or cannula 16 with an inner lumen 17, a distal portion 18, and a proximal portion 19 with a handle 20. A releasable distal plug 21 and the press-formed markers 10 are shown disposed within the inner lumen 17. A marker body 22 formed of a bioabsorbable material other than a polysaccharide with a radiopaque element is disposed between at least two press-formed marker bodies 10. A plunger 23 is slidably disposed within the inner lumen 17 and is provided with a head 24 on the proximal end 25 configured to allow an operator to press the plunger further into the inner lumen and push both the releasable plug 21 and marker members 10 and marker body 22 out of the discharge port or opening 26 in the distal end 27 of delivery cannula 16. Cannula handle 20 allows an operator to hold the cannula steady while pressing plunger 23 to discharge the releasable plug 21 and marker members 10 and marker body 22.

Releasable plug 21, preferably formed of polyethylene glycol, may substantially fill the discharge opening 26, as shown in FIG. 4 or at least occupy or block a portion of the discharge opening. The exposed face of plug 21 is preferably provided with an inclined configuration. Releasable plug 21 is configured to be tight enough, e.g. press fit, in the inner lumen 17 to prevent its inadvertent release which might allow premature discharge of marker 10 from delivery cannula 16, but the plug must be easily released when the plunger 23 is pressed deeper into the inner lumen 17 of the delivery cannula 16. An adhesive or mechanical element(s) may be used to hold the releasable plug 21 in a position within the inner lumen 17 to occlude the discharge opening 26. Suitable adhesives include polyurethane or polyacrylic based adhesives, polyhydroxymethacrylate base adhesives, fibrin glue (e.g., Tisseal™), collagen adhesive, or mixtures thereof. Suitable mechanical means for securing the releasable plug 21 are described in application Ser. No. 10/174,401, now U.S. Pat. No. 7,651,505. The distal end 26 of the delivery cannula 16 is provided with a ramp 27 which guides the discharged plug 21 and marker member 10 out of the side port 28 into the target site. The distal tip 29 may be tapered for delivery through a guide tube (not shown).

The delivery cannula 16 may be provided with markings 30 which serve as visual landmarks to aid an operator in accurately placing the distal portion 18 of the cannula 16 in a desired location within a patient's body for discharging the marker 10.

The exterior of the delivery cannula 16 is preferably configured to fit within a guide cannula sized to accept a Seno-Cor®, EnCor™, Mammotome® or Tru-Cut®, biopsy device. Typically, plug 21 and marker member 10 will have diameters determined by the size of the inner lumen 17 and typically will be about 0.02 inch (0.5 mm) to about 0.5 inch (12 mm), preferably about 0.04 inch (1 mm) to about 0.3 inch (8 mm) Plug 21 may have slightly larger transverse dimensions to provide a tight fit.

When the marker member 10 contacts body fluid within a body cavity such as a lumpectomy or biopsy site, the binding agent is dissolved and the polysaccharide draws moisture away from the blood and other fluids at the site and the clotting cascade begins to form thrombus at the site resulting in hemostasis.

While one or more particular forms of the invention have been illustrated and described herein in the context of a breast biopsy site, it will be apparent that the device and methods having features of the invention may find use in a variety of locations and in a variety of applications, in addition to the human breast, where tissue has been removed. Moreover, various modifications can be made without departing from the spirit and scope of the invention. For example, while the polysaccharide bodies are primarily described herein as press-formed bodies, the polysaccharide materials by be encapsulated in a bioabsorbable body or be in other forms. Accordingly, it is not intended that the invention be limited to the specific embodiments illustrated. It is therefore intended that this invention to be defined by the scope of the appended claims as broadly as the prior art will permit, and in view of the specification if need be. Moreover, those skilled in the art will recognize that features shown in one embodiment may be utilized in other embodiments. Additional details of pellet or other marker members and delivery systems may be found in application Ser. No. 10/753,694, filed on Jan. 7, 2004, and Ser. No. 10/976,138, filed on Oct. 27, 2004.

Terms such as "element", "member", "device", "section", "portion", "step", "means" and words of similar import when used in the following claims shall not be construed as invoking the provisions of 35 U.S.C. §112(6) unless the following claims expressly use the term "means" followed by a particular function without specific structure or expressly use the term "step" followed by a particular function without specific action. All patents and patent applications referred to above are hereby incorporated by reference in their entirety.

What is claimed is:

1. A method for treating a site within a patient from which tissue has been removed, comprising:
    providing at least one press-formed marker body formed of polysaccharide and a suitable binder, wherein each of the at least one press-formed marker body is formed of a mixture of 65% (by wt.) powder of corn starch or potato starch and 35% (by wt.) methylcellulose binder; and
    placing the at least one of the press-formed marker body within the site where tissue has been removed so as to provide hemostasis therein.

2. The method of claim 1, wherein the powder has a particle size less than 0.01 inch.

3. The method of claim 1, wherein the powder has a particle size of about 10 to about 200 micrometers.

4. The method of claim 1, wherein each of the at least one press-formed body has a transverse dimension of about 0.02 to about 0.1 inch.

5. The method of claim 1, wherein each of the at least one press-formed body has a transverse dimension of about 0.035 to about 0.075 inch.

6. The method of claim 1, wherein each of the at least one press-formed body has a length of about 0.1 to about 0.4 inch.

7. The method of claim 1, wherein each of the at least one press-formed body has a length of about 0.15 to about 0.35 inch.

8. The method of claim 1, wherein the at least one press-formed marker body is included in a plurality of marker elements disposed within an inner lumen of a tubular delivery member and the plurality of marker elements are urged out a discharge port in the tubular delivery member.

9. The method of claim 1, comprising a delivery tube with an inner lumen and a discharge port, and a plunger slidably disposed within the inner lumen of the delivery tube, the plunger having a proximal end and a distal end, the proximal end having a head configured to allow an operator to move the plunger within the inner lumen, and having the at least one press-formed marker body disposed in the inner lumen distal to the distal end of the plunger and a releasable plug positioned in the discharge port, further comprising moving the plunger in a distal direction to push all of the at least one press-formed marker body and the releasable plug out of a discharge port and into the site within the patient.

10. A method for use in treating a site within a patient from which tissue has been removed, comprising providing for application at the site at least one unitary marker pellet formed of polysaccharide powder and a suitable binder pressed into a desired shape, wherein each of the at least one press-formed marker body is formed of a mixture of 65% (by wt.) powder of corn starch or potato starch and 35% (by wt.) methylcellulose binder, the mixture being placed in a pellet die and subjected to pressure to form a unitary marker pellet.

11. The method of claim 10, comprising placing each individual unitary marker pellet formed of polysaccharide powder within the site where tissue has been removed so as to provide hemostasis therein.

12. A method to facilitate treating a site within a patient from which tissue has been removed, comprising:
   providing a plurality of marker members, each marker member of the plurality of marker members comprising a press-formed marker body formed of bioabsorbable polysaccharide and a binder, the bioabsorbable polysaccharide being in sufficient amounts to exhibit hemostatic properties, wherein at least one of the plurality of marker members is formed of a mixture of 65% (by wt.) powder of corn starch or potato starch and 35% (by wt.) methylcellulose binder, the plurality of marker members being disposed within an inner lumen of a tubular delivery member; and
   placing the plurality of marker members in a lumen of a delivery tube configured to deliver the plurality of marker members into the site within the patient from which the tissue has been removed.

* * * * *